United States Patent
Lindqvist et al.

(10) Patent No.: US 6,371,117 B1
(45) Date of Patent: Apr. 16, 2002

(54) DIRECTIONAL VALVE

(75) Inventors: Björn Lindqvist, Lidingö; Christian Rossby, Sundbyberg, both of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/328,466

(22) Filed: Jun. 9, 1999

(30) Foreign Application Priority Data

Jun. 15, 1998 (SE) .............................................. 9802123

(51) Int. Cl.[7] .............................................. A62B 18/01
(52) U.S. Cl. .............................. 128/207.12; 128/205.24
(58) Field of Search ........................ 128/205.18, 205.24, 128/204.18, 207.12, 200.29, 203.29; 137/907, 908, 855, 533.17

(56) References Cited

U.S. PATENT DOCUMENTS

| | | | | |
|---|---|---|---|---|
| 675,622 A | * | 6/1901 | Clinton ...................... | 137/533 |
| 1,156,837 A | * | 10/1915 | Doan .......................... | 137/533 |
| 1,657,741 A | * | 1/1928 | Carrey ....................... | 137/533 |
| 2,520,771 A | * | 8/1950 | Martin et al. ............ | 137/533.17 |
| 2,960,994 A | * | 11/1960 | Shaffer ..................... | 137/533 |
| 3,158,153 A | * | 11/1964 | Bloom et al. ............ | 128/142 |
| 3,219,030 A | * | 11/1965 | Bartlett, Jr. ............. | 128/203.11 |
| 3,247,866 A | * | 4/1966 | Sanz ......................... | 137/533 |
| 3,670,757 A | * | 6/1972 | Quian ....................... | 137/103 |
| 3,788,071 A | * | 1/1974 | Brewer ...................... | 137/533 |
| 3,871,373 A | * | 3/1975 | Jackson ..................... | 128/193 |
| 4,190,045 A | * | 2/1980 | Bartels ...................... | 128/205.24 |
| 4,232,706 A | * | 11/1980 | Ericson ..................... | 137/533 |
| 4,249,528 A | * | 2/1981 | Mathes ..................... | 128/205.13 |
| 4,499,916 A | * | 2/1985 | Hanson et al. ........... | 137/103 |
| 4,527,558 A | * | 7/1985 | Hoenig .................... | 128/205.24 |
| 4,558,708 A | * | 12/1985 | Labuda et al. ........... | 128/207.14 |
| 4,575,042 A | * | 3/1986 | Grimland et al. ........ | 251/46 |
| 4,622,964 A | * | 11/1986 | Flynn ....................... | 128/205.24 |
| 4,699,137 A | | 10/1987 | Schroeder | |
| 4,712,580 A | * | 12/1987 | Gilman et al. ............ | 137/908 |
| 4,830,047 A | * | 5/1989 | Hodge ...................... | 137/907 |
| 5,020,532 A | | 6/1991 | Mahoney et al. | |
| 5,176,658 A | | 1/1993 | Ranford | |
| 5,189,877 A | * | 3/1993 | Wells et al. .............. | 137/533 |
| 5,205,820 A | * | 4/1993 | Kriesel ..................... | 604/85 |
| 5,379,762 A | * | 1/1995 | Kobayashi ............... | 128/201.28 |
| 5,408,995 A | * | 4/1995 | Contino et al. ........... | 128/205.25 |
| 5,456,249 A | * | 10/1995 | Kirk ......................... | 128/205.13 |
| 5,501,214 A | * | 3/1996 | Sabo ......................... | 128/205.24 |
| 5,562,093 A | * | 10/1996 | Gerson ..................... | 128/203.11 |
| 5,575,279 A | * | 11/1996 | Beplate .................... | 128/203.11 |
| 5,630,409 A | * | 5/1997 | Bono et al. ............... | 128/200.18 |
| 5,630,411 A | * | 5/1997 | Holscher .................. | 128/205.24 |
| 5,653,223 A | * | 8/1997 | Pruitt ....................... | 128/200.21 |
| 5,653,226 A | * | 8/1997 | Heyer et al. ............. | 128/202.26 |
| 5,687,767 A | * | 11/1997 | Bowers ..................... | 128/205.24 |
| 5,724,961 A | * | 3/1998 | Tistrand ................... | 128/205.24 |
| 5,735,265 A | * | 4/1998 | Flynn ....................... | 128/203.11 |
| 5,738,087 A | * | 4/1998 | King ........................ | 128/200.23 |
| 5,787,882 A | * | 8/1998 | Hamilton .................. | 128/205.24 |
| 5,813,401 A | * | 9/1998 | Radcliff elt al. ........ | 128/205.24 |
| 5,829,433 A | * | 11/1998 | Shigematsu et al. ... | 128/205.24 |
| 5,839,435 A | * | 11/1998 | Matsuoka et al. ...... | 128/205.24 |
| 5,878,743 A | * | 3/1999 | Zdrojkowski et al. . | 128/205.24 |
| 5,881,718 A | * | 3/1999 | Mortensen et al. ..... | 128/205.24 |
| 5,896,857 A | * | 4/1999 | Hely et al. .............. | 128/205.24 |
| 5,897,305 A | * | 4/1999 | Roddis .................... | 137/533.17 |
| 5,937,855 A | * | 8/1999 | Zdrojkowski et al. . | 128/205.24 |
| 5,950,623 A | * | 9/1999 | Michell ................... | 128/205.24 |
| 5,954,051 A | * | 9/1999 | Heinonen et al. ....... | 128/205.24 |
| 6,047,698 A | * | 4/2000 | Magidson et al. ...... | 128/207.12 |

(List continued on next page.)

*Primary Examiner*—John G. Weiss
*Assistant Examiner*—Teena Mitchell
(74) *Attorney, Agent, or Firm*—Schiff Hardin & Waite

(57) ABSTRACT

A directional valve for a breathing apparatus, such as an anaesthetic machine, has a valve seat with a valve port and a valve plate resting loosely on a valve seat. The valve plate has a soft, pliant area on its surface in contact with the valve seat and a relatively rigid area across the valve port.

4 Claims, 1 Drawing Sheet

U.S. PATENT DOCUMENTS

| | | | | |
|---|---|---|---|---|
| 6,058,933 A | * | 5/2000 | Good et al. | 128/205.24 |
| 6,065,948 A | * | 5/2000 | Brown | 137/533.19 |
| 6,067,984 A | * | 5/2000 | Piper | 128/205.24 |
| 6,073,630 A | * | 6/2000 | Adahan | 128/205.24 |
| 6,095,140 A | * | 8/2000 | Poon et al. | 128/204.26 |
| 6,116,233 A | * | 9/2000 | Denyer et al. | 128/200.18 |
| 6,293,279 B1 | * | 9/2001 | Schmidt et al. | 128/200.23 |

* cited by examiner

DIRECTIONAL VALVE

BACKGROUND OF THE INVENTION

1. Field of the Invention

The present invention relates to a directional valve of the type suitable for use in a breathing apparatus, the directional valve having a valve seat with a valve port and a valve plate resting loosely on the valve seat.

2. Description of the Prior Art

Directional valves are used in breathing apparatuses for e.g. controlling flow to and from the user of the apparatus (usually a patient) to prevent or minimize re-breathing of expired gas.

Special demands are made on these directional valves in anaesthetic machines. The valve must seal over a wide dynamic counter-pressure range, typically from 1–2 mbar up to 200 mbar. At the same time, it must open to allow the passage of a flow at low pressure differences, typically a few mbar. This corresponds to a total force of a few tenths of a newton on the valve plate. Valve opening must be as independent of moisture (present at high levels in anaesthetic machines) as possible.

The valve's components also must be capable of withstanding an aggressive environment (anaesthetic gases and autoclaving) and feature an environmentally and economically advantageous design.

SUMMARY OF THE INVENTION

An object of the present invention is to provide a directional valve which satisfies the aforementioned demands.

The above object is achieved in accordance with the principles of the present invention in a directional valve for a breathing apparatus having a valve seat with a valve port and a valve plate resting loosely on the valve seat, the valve plate having a soft, pliable area on its surface in contact with the valve seat, and a relatively stiff area extending across the valve port.

By using a valve plate with a soft and pliable area in contact with the valve seat, the latter can be devised with less surface precision. As a result, more economical materials and fabrication procedures, such as injection molded plastic, can be used. The stiffer area across the valve port keeps the valve plate from being drawn or forced down into the valve port when large pressure differences prevail.

As the description above indicates, the valve plate must be very light. This is achieved in an embodiment wherein the valve plate is a membrane, with a thin, soft outer edge, whose thickness increases in toward the center of the membrane.

Alternatively, the valve plate can be a thin, soft membrane on which a rigid plate is attached to provide stiffness. The plate should not be too heavy.

DESCRIPTION OF THE PREFERRED EMBODIMENTS

Figure 1:
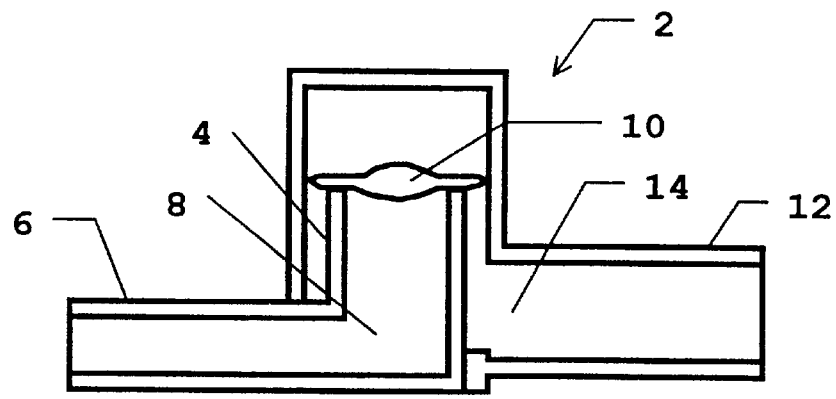
FIG. 1 shows an embodiment of a directional valve according to the invention.

FIG. 1 shows one embodiment of a directional valve 2 according to the invention. Tn this instance, the directional valve 2 is arranged in the flow path of an anaesthetic machine. The directional valve 2 comprises a valve seat 4, connected to an inlet 6 for the directional valve 2 (the inlet 6 can e.g. be one leg of a Y-piece connected to a patient). In principle, the valve seat 4 surrounds a valve port 8 with a specific flow-through area.

A valve plate 10 rests on the valve seat 4. In principle, this plate must be as light as possible (the maximum force against the valve seat, including the mass of the valve plate 10, must not exceed a few newtons), This is to ensure that the directional valve 2 will be able to open even when pressure differences are slight.

The valve seat is appropriately made from a hydrophobic material, e.g. compression molded plastic, to minimize the accumulation of fluid droplets on the area of contact between the valve seat 4 and the valve body 10. This fluid accumulation could otherwise cause the valve plate 10 to stick to the valve seat.

Gas flowing through the directional valve 2 exits through an outlet 12 via a second flow-through area 14. To keep the valve plate 10 from being misaligned by flowing gas, it is guided by the walls of its enclosure.

The valve plate 10 can be devised in different ways, as shown in FIGS. 2A and 2B and 3A and 3B. In addition to being light and able to open when pressure differences are slight, the valve plate must simultaneously be capable of withstanding high closing pressures.

Figures 2A, 2B:
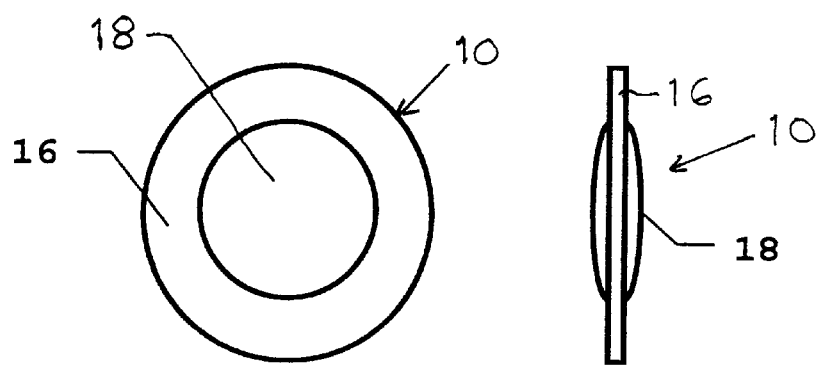
FIGS. 2A and 2B show a first embodiment of a valve plate, in a plan view and a side view, for use in the inventive directional valve.

FIGS. 2A and 2B show a first embodiment of the valve plate 10. Tn this instance, the valve plate 10 is homogeneously devised as a membrane with a thin, flat peripheral area 16 that provides a seal when the plate rests on the valve seat. The membrane's thickness increases towards the center, e.g. in the form of a convex bulge 18, thereby improving the stiffness of the valve plate 10. The thin outer area 16 is flexible and pliant enough to form a seal, even when the surface of the valve seat is somewhat uneven.

Figures 3A, 3B:
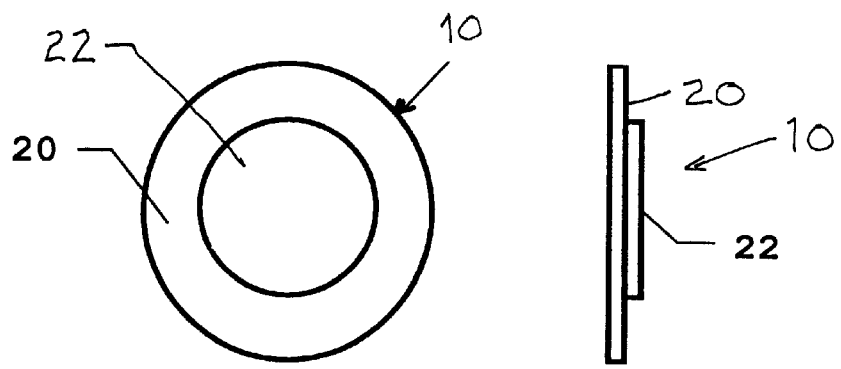
FIG. 3 show a second embodiment of a valve plate in a plan view and a side view, for use in the inventive directional valve.

Alternatively, the valve plate 10 can, as shown in FIGS. 3A and 3B, be made of two or more components. In this instance, the valve plate 10 is formed by a thin membrane 20 onto which a stiffening plate 22 is attached in any appropriate fashion.

Other designs for the valve plate are also possible. When the plate is made of a number of components, as shown in FIGS. 3A and 3B, some material and weight savings can be made if the membrane 20 is perforated. This perforation is covered by the stiffening plate 22.

Although modifications and changes may be suggested by those skilled in the art, it is the intention of the inventors to embody within the patent warranted hereon all changes and modifications as reasonably and properly come within the scope of their contribution to the art.

We claim as our invention:

1. A directional valve for a breathing apparatus, comprising:
   a valve seat surrounding a valve port;
   a valve plate resting unattached on said valve seat and thereby occluding said valve port; and
   said valve plate having a soft, pliable surface region in contact with said valve seat and a substantially stiff region spanning said valve port.

2. A directional valve as claimed in claim 1 wherein said valve plate comprises a circular membrane of soft material, said membrane having a peripheral annular region which is flat and which forms said soft, pliable region, and a convex central portion forming said substantially stiff region.

3. A directional valve as claimed in claim 1 wherein said valve plate comprises a flat, circular membrane of soft material, and a plate composed of material which is stiffer than said soft material disposed centrally on said circular membrane, said soft material forming said soft, pliable region and said plate forming said substantially stiffer region.

4. A directional valve as claimed in claim 1 wherein said valve seat is comprised of hydrophobic material.

* * * * *